United States Patent

Tsukada et al.

Patent Number: 6,059,761
Date of Patent: May 9, 2000

[54] SIMPLE AUTOMATIC OPENING AND CLOSING TYPE OF URINATION APPARATUS

[75] Inventors: Osamu Tsukada, Nagano-ken; Yasuhiko Nakajima, Kanagawa-ken, both of Japan

[73] Assignee: Tsukada Medical Research Co., Ltd., Tokyo, Japan

[21] Appl. No.: 09/117,086

[22] PCT Filed: Nov. 27, 1996

[86] PCT No.: PCT/JP96/03465

§ 371 Date: Jul. 23, 1998

§ 102(e) Date: Jul. 23, 1998

[87] PCT Pub. No.: WO98/23309

PCT Pub. Date: Jun. 4, 1998

[51] Int. Cl.[7] .................................................. A61M 1/00
[52] U.S. Cl. .......................... 604/317; 604/327; 600/573
[58] Field of Search .................................. 604/317, 327, 604/328, 329, 331, 349; 600/573, 574, 577

[56] References Cited

U.S. PATENT DOCUMENTS

| | | | |
|---|---|---|---|
| 5,437,652 | 8/1995 | Anatolievich | 604/349 |
| 5,776,077 | 7/1998 | Kottig | 600/573 |
| 5,797,855 | 8/1998 | Hazard et al. | 600/513 |

FOREIGN PATENT DOCUMENTS

| | | |
|---|---|---|
| 60-80459 | 5/1985 | Japan . |
| 60-212168 | 10/1985 | Japan . |

*Primary Examiner*—Corrine McDermott
*Assistant Examiner*—David J. Cho
*Attorney, Agent, or Firm*—Sughrue, Mion, Zinn, Macpeak & Seas, PLLC

[57] ABSTRACT

A simple automatic opening and closing type of urination apparatus (10) comprises a cylinder (2), a pressure responsive plunger (3), a resilient member (4), a protective casing (5), and a lock mechanism (6). The cylinder (2) is provided in a front end with an inlet port (21), on a rear end with a cylinder flange (22), and in an outer peripheral wall of an intermediate portion with a plurality of outlet ports (23). The pressure responsive plunger (3) is slidably received in the cylinder (2) and provided on a front end with a liquid-sealing portion (31), on a rear end with a plunger flange (32), and on an intermediate portion with a plurality of ribs (33) which extend longitudinally and cross each other radially. At least one of the ribs (33) is provided with serrated teeth (331) which are aligned at a given pitch in a longitudinal direction. The resilient member (4) interconnects the cylinder flange (22) on the rear end of the cylinder (2) and the plunger flange (32) on the rear end of the plunger (3) to attract the ends to each other. The protective casing (5) is secured to the rear end of the cylinder (2) for permitting the pressure responsive plunger (3) to move in an axial direction. The lock mechanism (6) engages with and disengages from the serrated tooth (331) of the rib (33) of the plunger (3) to retain and release the axial movement of the plunger (3). The urine in a urinary bladder (12) is discharged from one of the outlet ports (23) in the cylinder (2) into a urine-collecting bag (14) outside of a patient's body when a pressure of urine in the urinary bladder reaches one of predetermined values. Each of the outlet ports (23) is set to correspond to each of the predetermined values of the pressure of urine in the urinary bladder (12) communicated with the inlet port of the cylinder (2).

11 Claims, 7 Drawing Sheets

SIMPLE AUTOMATIC OPENING AND CLOSING TYPE OF URINATION APPARATUS

TECHNICAL FIELD

This invention relates to a simple automatic opening and closing type of urination apparatus which is easily connected between a catheter and a urine-collecting bag and which encourages automatically urination and urine-storage of a urinary bladder of a patient who carries out urination by inserting the catheter into the urinary bladder.

BACKGROUND OF THE INVENTION

It is necessary for a patient, who is imperfect or disable in urination, to discharge urine out of the body through a urethra catheter left in the urinary bladder. To this end, several kinds of urination apparatus have been utilized. Most of conventional urination apparatuses introduce urine into the urine-collecting bag through a urethra catheter inserted through the ureter into the urinary bladder and an on-off valve connected to an end of the urethra catheter. In such a urination apparatus, since the urine always flows out of the body through the catheter left in the urinary bladder, the bladder does not effect expansion and contraction to accomplish natural urine-storage and urination and thus remains in an atrophied state. Consequently, the urinary bladder may lose its function after a long period of time.

Thus, several automatic urination apparatuses which actuate an on-off valve in response to detection of a urine pressure in the urinary bladder have been proposed to maintain the function of the urinary bladder. However, these apparatuses have several problems in that they are large in scale, expensive, and inconvenient for a patient.

SUMMARY OF THE INVENTION

An object of the present invention is to provide a simple automatic opening and closing type of urination apparatus which enables a patient to collect urine while maintaining a normal function of a urinary bladder and is inexpensive and simple in construction.

A simple automatic opening and closing type of urination apparatus in accordance with the present invention, comprises a cylinder, a pressure responsive plunger, a resilient member, a protective casing, and a lock mechanism.

The cylinder is provided in a front end with an inlet port, on a rear end with a cylinder flange, and in an outer peripheral wall of an intermediate portion with a plurality of outlet ports. The pressure responsive plunger is slidably received in the cylinder and provided on a front end with a liquid-sealing portion, on a rear end with a plunger flange, and on an intermediate portion with a plurality of ribs which extend longitudinally and cross each other radially. At least one of the ribs is provided with serrated teeth which are aligned at a given pitch in a longitudinal direction. The resilient member interconnects the cylinder flange on the rear end of the cylinder and the plunger flange on the rear end of the plunger to attract the ends to each other. The protective casing is secured to the rear end of the cylinder for permitting the pressure responsive plunger to move in an axial direction. The lock mechanism engages with and disengages from the serrated teeth of the rib of the plunger to retain and release the axial movement of the plunger.

The urine in a urinary bladder is discharged from one of the outlet ports in the cylinder into a urine-collecting bag outside a patient's body when a pressure of urine in the urinary bladder reaches one of predetermined values. Each of the outlet ports is set to correspond to each of the predetermined values of the pressure of urine in the urinary bladder communicated with the inlet port of the cylinder. After completing urination, the above operation is repeated. Thus, the uninary bladder can expand and contract for urine-storage and urination as usual, although the uninary bladder is communicated with the urine-collecting bag through the catheter.

Also, in the urination apparatus of the present invention, preferably, three outlet ports are provided in the cylinder in an axial direction to select one of low, middle, and high pressures of urine in the urinary bladder.

Although it is necessary to provide a plurality of ribs on the pressure responsive plunger, four ribs may be provided on the pressure responsive plunger to cross each other at an axis in a cruciform shape in order to make it easy to form the ribs.

A given rib out of the ribs is provided with serrated teeth. The lock mechanism is attached to a front end of the casing. The lock mechanism includes a pawl member and a support member. The pawl member includes a pawl portion which brings the pawl member into engagement with the serrated teeth of the rib in the protective casing and a lever portion which is held on the support member outside of the casing and serves to move the pawl portion in a radial direction.

Four ribs may be provided on the pressure responsive plunger to cross each other at an axis in a cruciform shape. A pair of the ribs on a given diameter may be provided with serrated teeth. The lock mechanism is attached to a front end of the casing. The lock mechanism includes a pawl member and a support member. The pawl member includes a pawl portion which brings the pawl member into engagement with the serrated teeth of the rib in the protective casing and a lever portion which is held on the support member outside of the casing and serves to move the pawl portion in a radial direction.

A pair of ribs on a given diameter or tour ribs may be provided with serrated teeth. The lock mechanism is attached to a front end of the casing. The lock mechanism includes a pawl member and a ring-like support member. The ring-like support member is mounted on an outer periphery of the protective casing slidably in a circumferential direction. The pawl member includes a pawl portion which brings the pawl member into engagement with the serrated teeth of the rib in the protective casing and a holding portion fixed on the ring-like support member outside of the protective casing.

DESCRIPTION OF THE PREFERRED EMBODIMENTS

Figure 1:
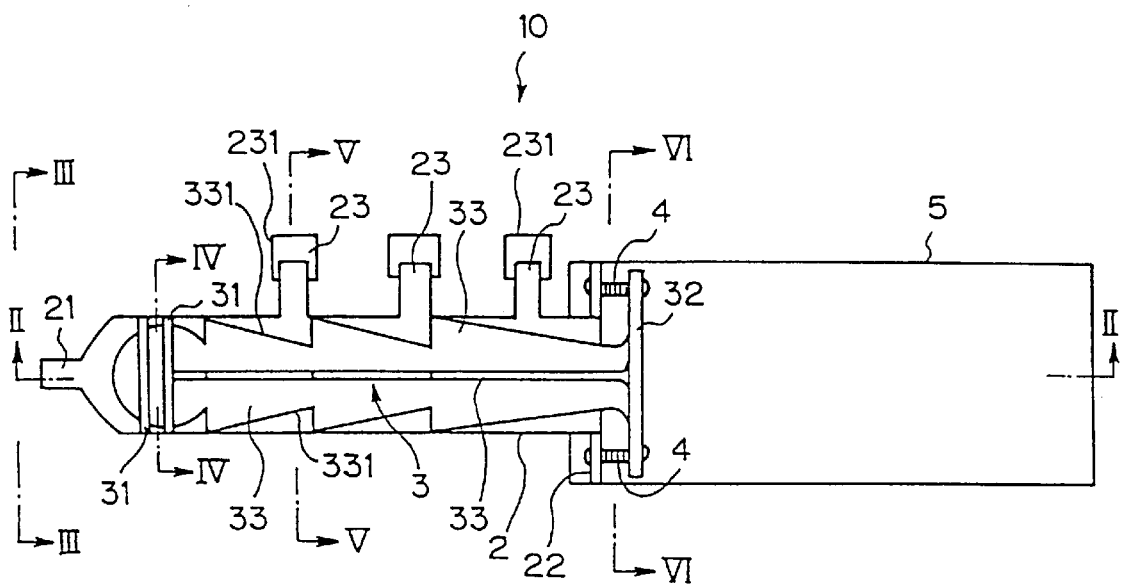
FIG. 1 is a longitudinal sectional view of a simple automatic opening and closing type of urination apparatus in accordance with the present invention.

Embodiments of a simple automatic opening and closing type of urination apparatus in accordance with the present invention will be explained below by referring now to the drawings.

As shown in FIGS. 1 through 6, a simple automatic opening and closing type of urination apparatus 10 comprises a cylinder 2, a pressure responsive plunger 3, a resilient member 4, a protective casing 5, and a lock mechanism 6.

The cylinder 2 is made of a plastic material and is provided in a front end with an inlet port 21, on a rear end with a cylinder flange 22, and in an outer peripheral wall of an intermediate portion with a plurality of outlet ports 23. A rubber cap 231 is detachably attached to a distal end of each outlet port 23. In the illustrated embodiment, three outlet ports 23 are provided, for example, to associate with urine pressures of 50 mmHg, 120 mmHg, and 200 mmHg from the distal end to the proximal end of the cylinder 2.

The pressure responsive plunger 3 is made of a plastic material and is slidably received in the cylinder 2. The plunger 3 is provided on a front end with a liquid-sealing portion 31, on a rear end with a plunger flange 32, and on an intermediate portion with a plurality of ribs 33 (four ribs in the illustrated embodiment) which extend longitudinally and cross each other radially. In an injector unit sold commercially, a rib type plunger usually has four ribs. Thus, the plunger can be available cheaply. At least one of the ribs 33 is provided with serrated teeth 331 which are aligned at a given pitch in a longitudinal direction. The serrated teeth 331 are arranged in association with the set positions of the lock mechanism 6 described below. In the illustrated embodiment, the serrated teeth 331 are provided on all four ribs 33 for convenience of explanation and production.

Figure 2:
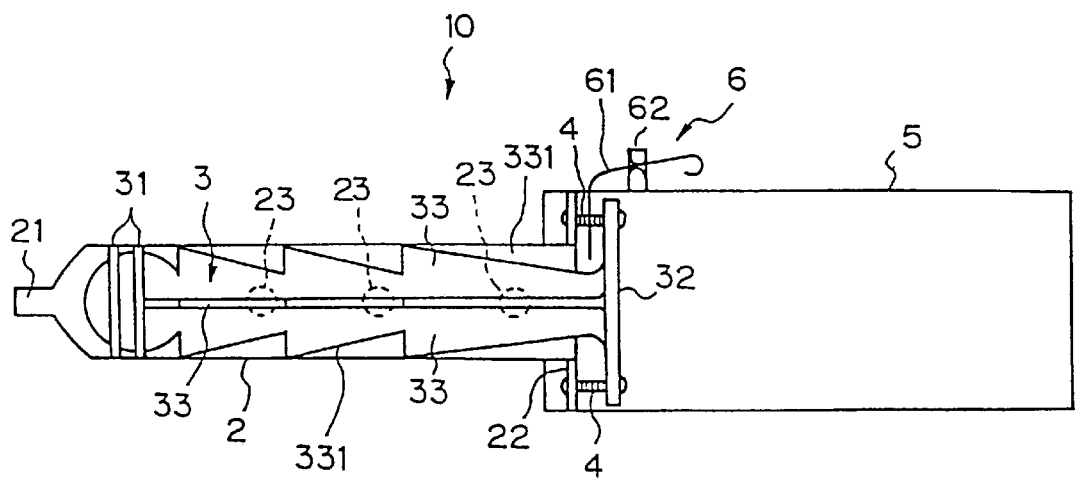
FIG. 2 is a longitudinal sectional view of the urination apparatus taken along a line II—II in FIG. 1.
Figure 3:
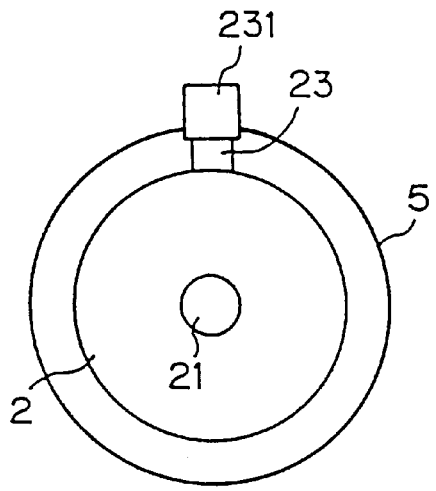
FIG. 3 is a front elevational view of the urination apparatus taken along a line III—III in FIG. 1.
Figure 4:
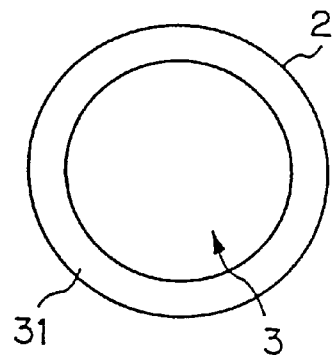
FIG. 4 is a cross sectional view of the urination apparatus taken along a line IV—IV in FIG. 1.
Figure 5:
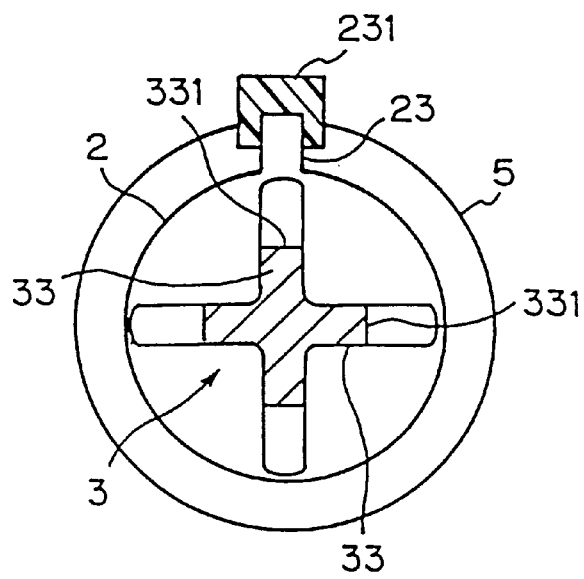
FIG. 5 is a cross sectional view of the urination apparatus taken along a line V—V in FIG. 1.
Figure 6:
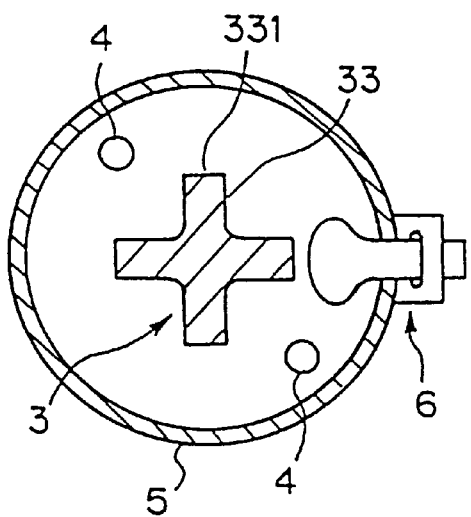
FIG. 6 is a cross sectional view of the urination apparatus taken along a line VI—VI in FIG. 1.

The serrated teeth 331, as shown in FIGS. 1 and 2, are provided with vertical surfaces opposed to a distal end of the pressure responsive plunger 3 (to a left side in the drawings) and with gentle slopes opposed to a proximal end of the plunger 3 (to a right side in the drawings).

The resilient member 4 interconnects the cylinder flange 22 on the rear end of the cylinder 2 and the plunger flange 32 on the rear end of the plunger 3 to attract the ends to each other.

The resilient member 4 may be a conventional member such as a tension coil spring, a rubber string, or the like.

The protective casing 5 is made of metal, plastic, wood, paper, or the like. The protective casing 5 is secured to the rear end of the cylinder 2 for permitting the pressure responsive plunger 3 to move in an axial direction.

The lock mechanism 6 engages with and disengages from the serrated teeth 331 of the rib 33 of the plunger 3 to retain and release the axial movement of the plunger 3.

Figure 12:
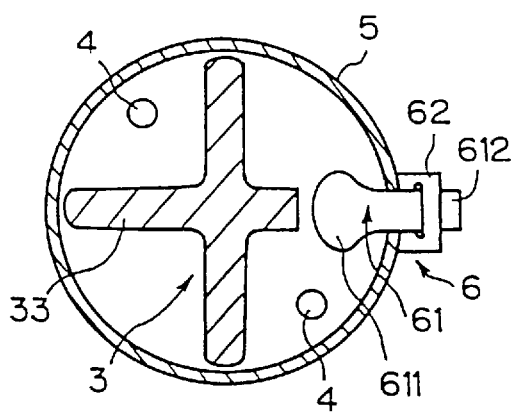
FIGS. 12(A) to (E) are cross sectional views corresponding to FIG. 6, illustrating various kinds of alteration of the urination apparatus of the present invention.
Figure 12:
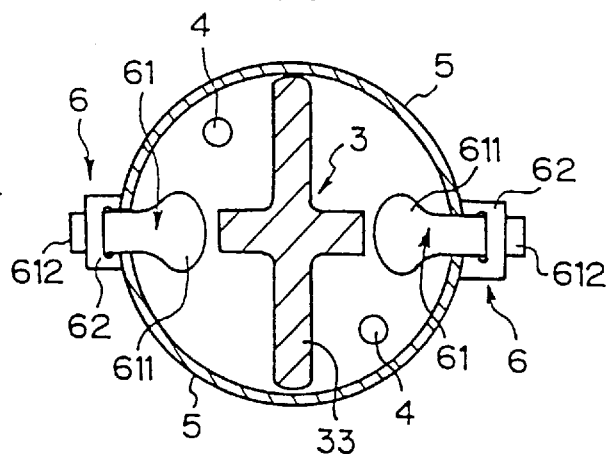
Figure 12:
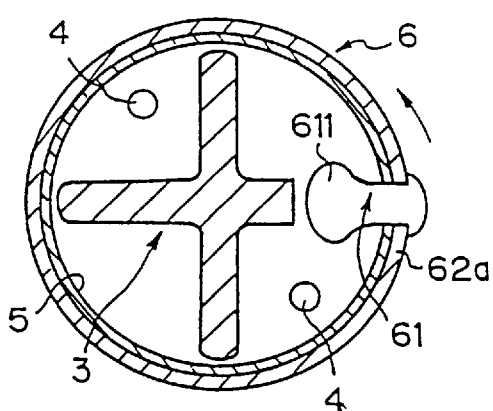
Figure 12:
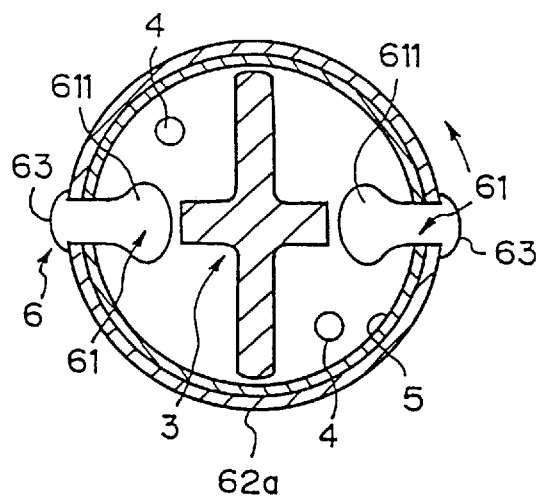
Figure 12:
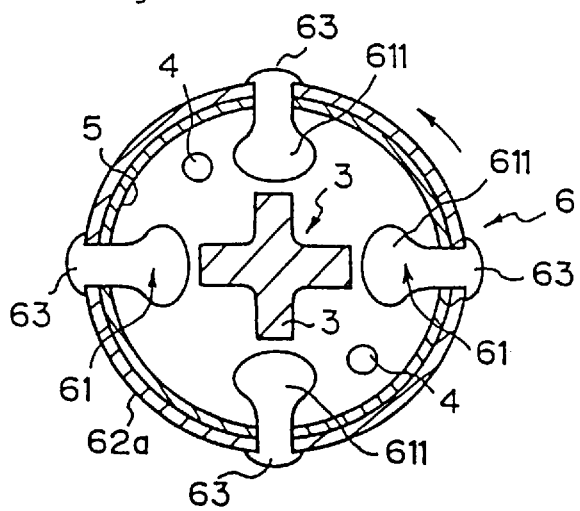

In the event that the plunger 3 is provided with four ribs 33, as shown in FIG. 12, the serrated teeth 331 may be formed on a given rib 33 ((A) and (C) in FIG. 12), on a pair of ribs 33 on a given diameter of the plunger 3 ((B) and (D) in FIG. 12), or on all four ribs 33((E)).

Figure 7:
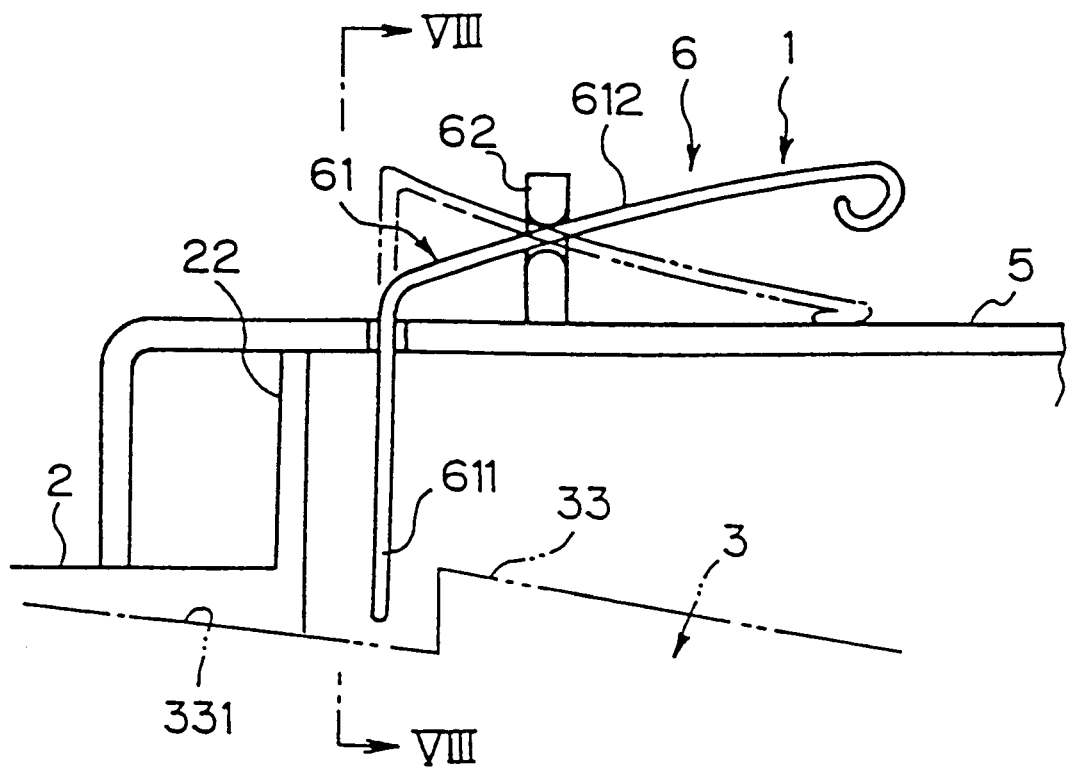
FIG. 7 is a partially enlarged view of a lock mechanism shown in FIG. 2.
Figure 8:
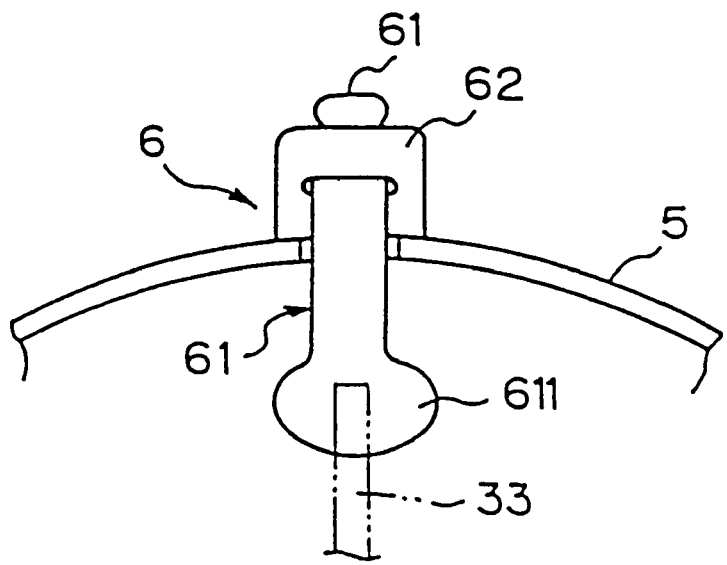
FIG. 8 is a front elevational view of the lock mechanism taken along a line VIII—VIII in FIG. 7.

The lock mechanism 6, as shown in FIGS. 2, 7, and 8, is attached to a front end of the protective casing 5. The lock mechanism 6 includes a pawl member 61 and a support member 62. The pawl member 61 includes a pawl portion 611 which brings the pawl member 61 into engagement with the serrated tooth 331 of the rib 33 in the protective casing 5 and a lever portion 612 which is held on the support member 62 outside of the casing 5 and serves to move the pawl portion 611 in a radial direction.

When the lever portion 612 of the pawl member 61 is manually pushed down in FIG. 7, the lever portion 612 is moved to a position shown by two-dot chain lines in FIG. 7. This displacement releases an engagement between the pawl member 611 and the serrated tooth 331 on the rib 33. When the lever portion 612 is released from the pushing force, the lever portion 612 returns to a position shown by solid lines in FIG. 7.

In the case of such a lever type lock mechanism 6, it may be provided on only one position on a periphery of the protective casing 5((A) in FIG. 12) or on two opposite positions on a diameter of the casing 5((B) in FIG. 12).

As shown in (C), (D), and (E) in FIG. 12, the lock mechanism 6 may include a pawl member 61 and a ring-like support member 62a. The ring-like support member 62a is mounted on an outer periphery of the protective casing 5 slidably in a circumferential direction. The pawl member 61 includes a pawl portion 611 which brings the pawl member 61 into engagement with the serrated tooth 331 of the rib 33 in the protective casing 5 and a holding portion 63 fixed on the ring-like support member 62a outside of the protective casing 5.

In the case of such a ring type lock mechanism 6, it may be provided on only one position on a periphery of the protective casing 5 ((C) in FIG. 12), on two positions on the periphery and on a diameter of the casing 5 ((D) in FIG. 12), or four positions on the periphery and two cross diameters of the casing 5 ((E) in FIG. 12).

In the ring type lock mechanism 6, the plural pawl members 61 can be rotated at the same time by sliding the ring-like support member 62a on the protective casing 5 by a given angle (for example, 45°) in a circumferential direction.

At least the pawl portion 611 of the pawl member 61 preferably has a resilient function.

The lock mechanism 6 may include a combination of projections and recesses, a combination of magnets, or a combination of balls and springs as well as the mechanisms described above.

Next, an operation of the embodiment of the simple automatic opening and closing type of urination apparatus in accordance with the present invention will be described below by referring to FIGS. 9 to 11.

Figure 9:
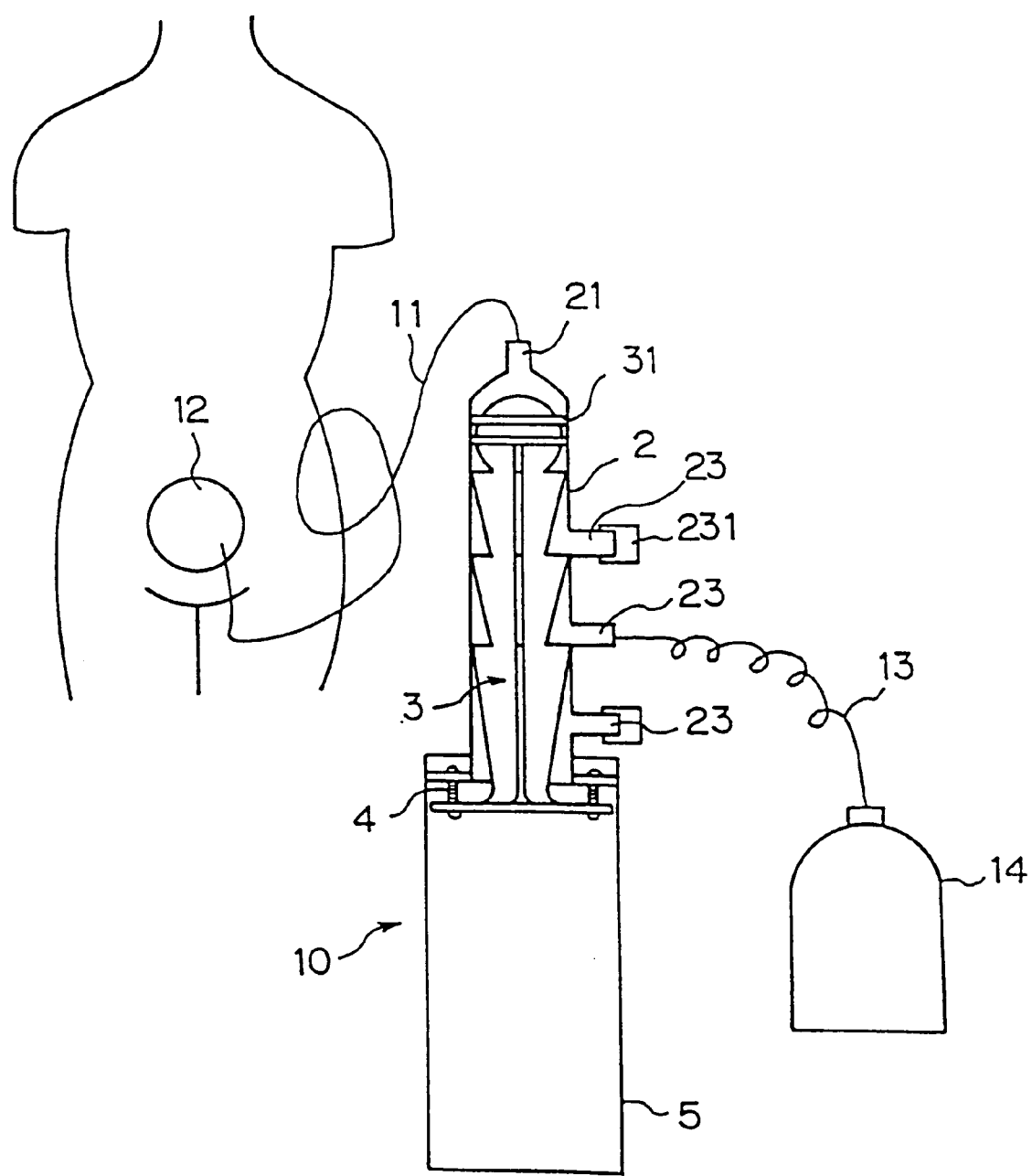
FIG. 9 is a schematic explanatory view of a using example of the urination apparatus of the present invention.
Figure 10:
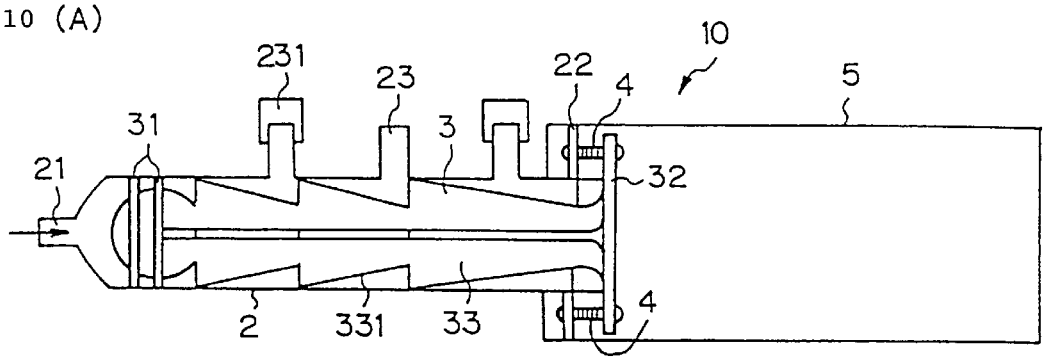
FIGS. 10(A) to (D) are longitudinal sectional views substantially similar to FIG. 1, illustrating an operation of the urination apparatus of the present invention.
Figure 10:
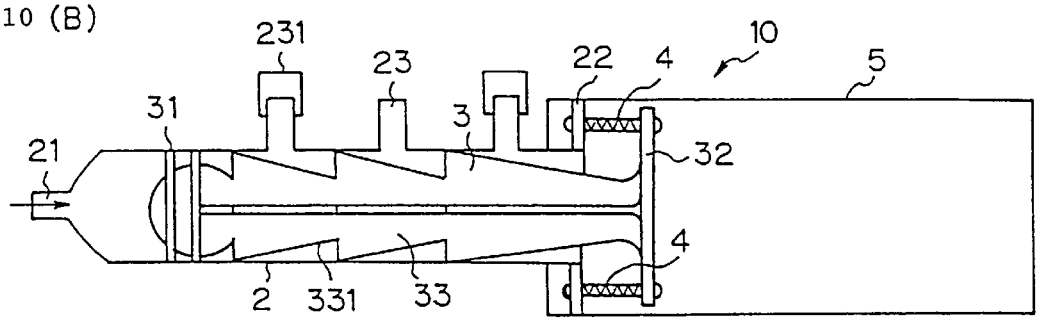
Figure 10:
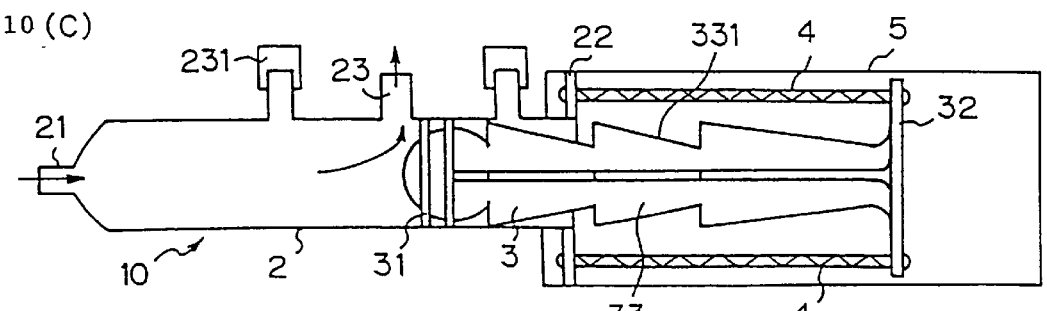
Figure 10:
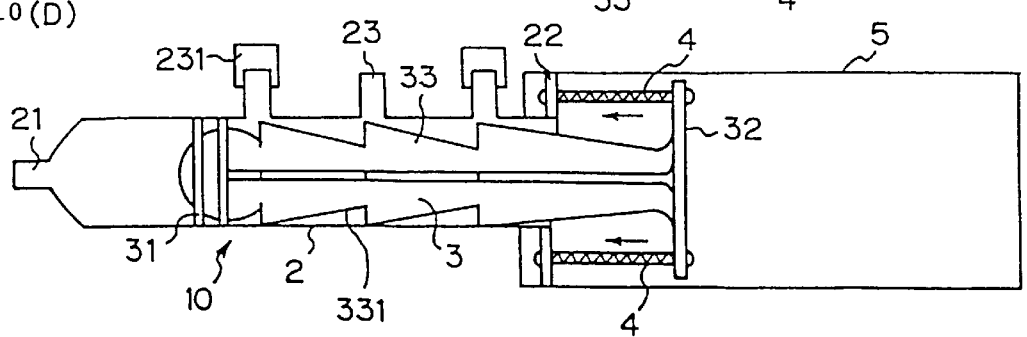

As shown in FIG. 9, an inlet port 21 in the distal end of the cylinder 2 of the urination apparatus 10 of the present invention 10 is communicated with a uninary bladder 12 in a human body through a conventional catheter 11. An outlet port 23 is selected out of plural outlet ports 23 in an intermediate outer peripheral wall of the cylinder 2. The selected outlet port 23 is communicated through a conduit 13 with a urine-collecting bag 14. The other outlet ports 23 are closed by caps 231.

In the illustrated embodiment, the cylinder 2 is provided with three outlet ports 23 along an axial direction of the cylinder 2 so as to select one of low, middle, and high urine pressures in the urinary bladder 12. For example, the outlet ports 23 of the cylinder 2 from the front end to the rear end are set to select the urine pressures of 50 mmHg, 120 mmHg, and 200 mmHg, respectively. The position of each outlet port 23 in the cylinder 2 depends on a resistant force exerted in the resilient member 4.

Usually, a volume in a human urinary bladder is about 300 to 400 ml in maximum and a urination pressure is about 50 to 400 mmHg in maximum. However, since the volume and pressure are different due to personal sex, age, disease, and the like, it is preferable to select the outlet port 23 in accordance with a personal situation.

In the set condition shown in FIG. 9, when urine is stored in the urinary bladder 12 and the urine pressure reaches, for example, 120 mmHg, the pressure responsive plunger 3 is pushed out of the cylinder 2 into the protective casing 5. When the liquid sealing portion 31 of the plunger 3 passes over the selected outlet port 23 (central outlet port 23 for 120 mmhg), the urine is discharged through the outlet port 23 into the urine-collecting bag 14. Although the urine pressure in the cylinder 2 is lowered in association with the discharge of urine, the lock mechanism 6 (see FIG. 2) locks the pressure responsive plunger 3, thereby preventing the plunger 3 from retracting toward the inlet port 21.

After completing the discharge of urine, if the lock mechanism 6 is released, the pressure responsive plunger 3 returns to the original position by a recovery force of the resilient member 3.

After discharging the urine, the above process will be repeated again. Thus, the urinary bladder 12 can repeat expansion and contraction to do natural urine-storage and urination, even if the urinary bladder 12 is communicated through the catheter 12 with the urine-collecting bag 14.

The operation described above will be explained in more detail by referring to FIGS. 10 and 11. FIGS. 10(A) to (D) substantially correspond to FIG. 1 and are longitudinal sectional views of the urination apparatus of the present invention. FIGS. 11(A) to (D) substantially correspond to FIG. 2 and FIGS. 10(A) to (D) and are longitudinal sectional views.

Figure 11A:
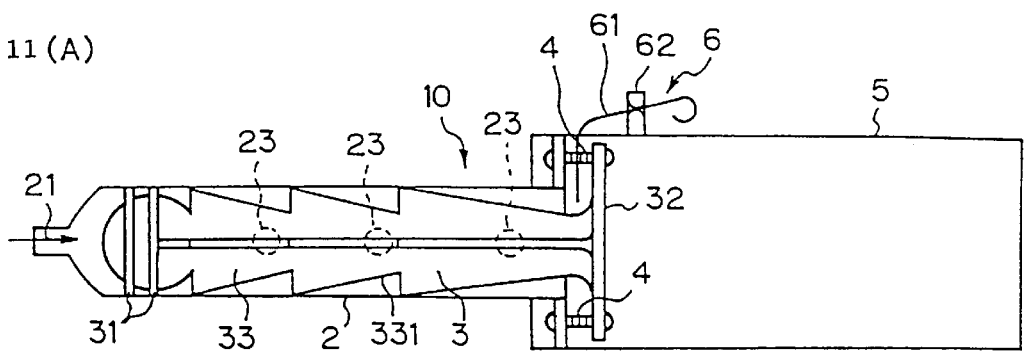
FIGS. 11(A) to (D) are longitudinal sectional views substantially similar to FIG. 2 and corresponding to FIGS. 10(A) to (D), illustrating an operation of the urination apparatus of the present invention.

As shown in FIG. 10(A) and FIG. 11(A), the central outlet port 23 of the cylinder 2 is selected and the cap 231 is detached from the port 23. The other caps 231 are attached to the other ports 23 as they are. The urine from the urinary bladder 12 flows through the inlet port 21 into the cylinder 2.

Figure 11B:
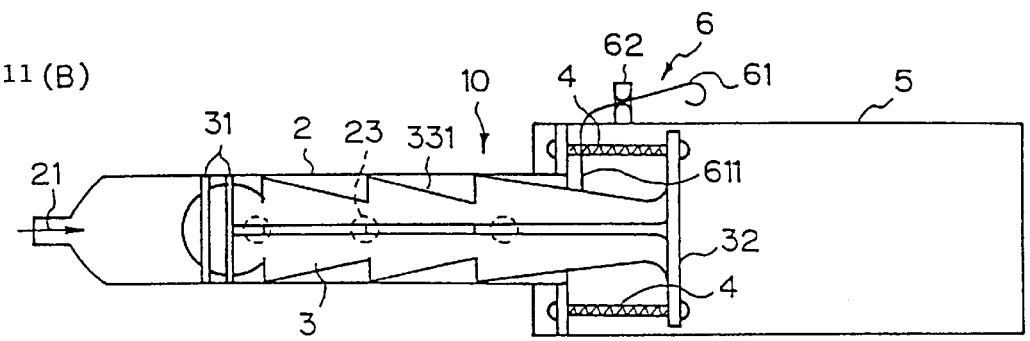

As shown in FIG. 10(B) and FIG. 11(B), the pressure responsive plunger 3 is pushed out to the right side in the drawings against the resilient resistance of the resilient member 4 by means of the urine pressure. The proximal end of the pressure responsive plunger 3 is protected by the protective casing 5. The pawl portion 611 of the pawl member 61 in the lock mechanism 6 rides on the gentle slope of the serrated tooth 331 of the rib 33 on the plunger 3 while being resiliently deformed.

Figure 11C:
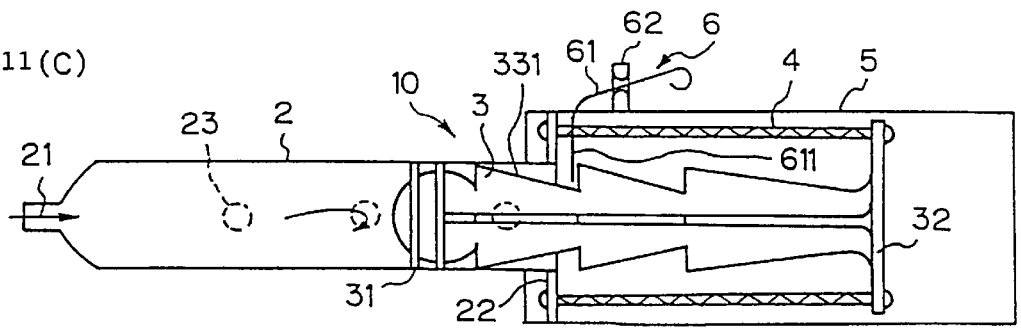

As shown in FIG. 10(C) and FIG. 11(C), when the liquid-sealing portion 31 of the pressure responsive plunger 3 passes over the central outlet port 23, the port 23 is opened to be communicated with the inlet port 21. Consequently, the urine is discharged through the outlet port 23 from the cylinder 2 into the urine-collecting bag 14. Although the urine pressure in the cylinder 2 is lowered in connection with the discharge of urine, the pawl portion 611 of the pawl member 61 in the lock mechanism 6 engages with the vertical surface of the serrated tooth 331 of the rib 33 on the pressure responsive plunger 3, thereby preventing the resilient member 4 from retracting the plunger 3.

Figure 11D:
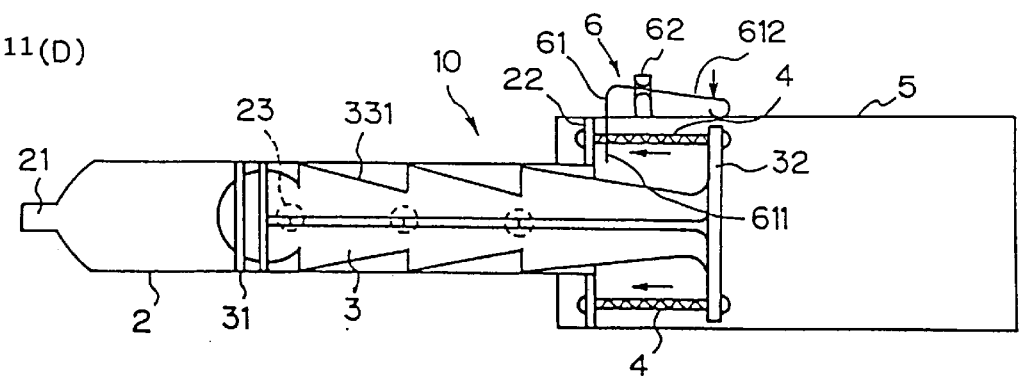

After confirming if the urination is completed, as shown in FIG. 10(D) and FIG. 11(D), when the lever portion 612 of the pawl member 61 in the lock mechanism 6 is manually pushed down, the pawl portion 611 is raised to disengage from the vertical surface of the tooth 331, thereby releasing the lock mechanism 6. Thus, the pressure responsive plunger 3 returns to the original position by means of the recovery force of the resilient member 4.

[Industrial Applicability]

The present invention can be applied to a case of injecting a liquid medicine into a human body although the present invention is utilized as a urination apparatus. Further, the present invention can be applied to a common fluid appliance as well as a medical appliance.

We claim:

1. A simple automatic opening and closing type of urination apparatus comprising:

a cylinder provided in a front end with an inlet port, on a rear end with a cylinder flange, and in an outer peripheral wall of an intermediate portion with a plurality of outlet ports;

a pressure responsive plunger slidably received in said cylinder and provided on a front end with a liquid-sealing portion, on a rear end with a plunger flange, and on an intermediate portion with a plurality of ribs which extend longitudinally and cross each other radially, at least one of said ribs being provided with serrated teeth which are aligned at a given pitch in a longitudinal direction;

a resilient member for interconnecting said cylinder flange on the rear end of said cylinder and said plunger flange on the rear end of said plunger to attract said ends to each other;

a protective casing secured to the rear end of said cylinder for permitting said pressure responsive plunger to move in an axial direction; and a lock mechanism for engaging with and disengaging from said serrated teeth of said rib of said plunger to retain and release the axial movement of said plunger;

whereby the urine in a urinary bladder is discharged from one of said outlet ports in said cylinder into a urine-collecting bag outside of a patient's body when a pressure of urine in the urinary bladder reaches one of predetermined values, each of said outlet ports being set to correspond to each of said predetermined values of said pressure of urine in the urinary bladder communicated with said inlet port of said cylinder.

2. A urination apparatus according to claim 1, wherein three outlet ports are provided in said cylinder in an axial direction to select one of low, middle, and high pressures of urine in the urinary bladder.

3. A urination apparatus according to claim 1, wherein four ribs are provided on said pressure responsive plunger to cross each other at an axis in a cruciform shape, one of said ribs is provided with serrated teeth, said lock mechanism is attached to a front end of said casing, said lock mechanism includes a pawl member and a support member, and said pawl member includes a pawl portion which brings said pawl member into engagement with said serrated tooth of said rib in said protective casing and a lever portion which is held on said support member outside of said casing and serves to move said pawl portion in a radial direction.

4. A urination apparatus according to claim 3, wherein three outlet ports are provided in said cylinder in an axial direction to select one of low, middle, and high pressures of urine in the urinary bladder.

5. A urination apparatus according to claim 1, wherein four ribs are provided on said pressure responsive plunger to cross each other at an axis in a cruciform shape, a pair of ribs on a given diameter are provided with serrated teeth, said lock mechanism is attached to a front end of said casing, said lock mechanism includes a pawl member and a support member, and said pawl member includes a pawl portion which brings said pawl member into engagement with said serrated tooth of said rib in said protective casing and a lever portion which is held on said support member outside of said casing and serves to move said pawl portion in a radial direction.

6. A urination apparatus according to claim 1, wherein four ribs are provided on said pressure responsive plunger to cross each other at an axis in a cruciform shape, one of said ribs is provided with serrated teeth, said lock mechanism is attached to a front end of said casing, said lock mechanism includes a pawl member and a ring-like support member, said ring-like support member is mounted on an outer periphery of said protective casing slidably in a circumferential direction, and said pawl member includes a pawl portion which brings said pawl member into engagement with said serrated tooth of said rib in said protective casing and a holding portion fixed on said ring-like support member outside of said protective casing.

7. A urination apparatus according to claim 6, wherein three outlet ports are provided in said cylinder in an axial direction to select one of low, middle, and high pressures of urine in the urinary bladder.

8. A urination apparatus according to claim 1, wherein four ribs are provided on said pressure responsive plunger to cross each other at an axis in a cruciform shape, a pair of said ribs on a given diameter are provided with serrated teeth, said lock mechanism is attached to a front end of said casing, said lock mechanism includes a pawl member and a ring-like support member, said ring-like support member is mounted on an outer periphery of said protective casing slidably in a circumferential direction, and said pawl member includes a pawl portion which brings said pawl member into engagement with said serrated tooth of said rib in said protective casing and a holding portion fixed on said ring-like support member outside of said protective casing.

9. A urination apparatus according to claim 8, wherein three outlet ports are provided in said cylinder in an axial direction to select one of low, middle and high pressures of urine in the urinary bladder.

10. A urination apparatus according to claim 1, wherein four ribs are provided on said pressure responsive plunger to cross each other at an axis in a cruciform shape, all of said four ribs are provided with serrated teeth, said lock mechanism is attached to a front end of said casing, said lock mechanism includes a pawl member and a ring-like support member, said ring-like support member is mounted on an outer periphery of said protective casing slidably in a circumferential direction, and said pawl member includes a pawl portion which brings said pawl member into engagement with said serrated tooth of said rib in said protective casing and a holding portion fixed on said ring-like support member outside of said protective casing.

11. A urination apparatus according to claim 10, wherein three outlet ports are provided in said cylinder in an axial direction to select one of low, middle and high pressures of urine in the urinary bladder.

* * * * *